United States Patent [19]

Piety et al.

[11] Patent Number: 5,386,117
[45] Date of Patent: Jan. 31, 1995

[54] INFRARED THERMOGRAPHY SYSTEM INCLUDING MOBILE UNIT

[75] Inventors: Kenneth R. Piety; Brian D. Heise; Rexford A. Battenberg, all of Knoxville; Willie T. King, Powell, all of Tenn.

[73] Assignee: Computational Systems Incorporated, Knoxville, Tenn.

[21] Appl. No.: 73,132

[22] Filed: Jun. 7, 1993

[51] Int. Cl.[6] .......................................... G01N 25/72
[52] U.S. Cl. .................... 250/330; 250/358.1
[58] Field of Search ............ 250/330, 332, 342, 358.1; 374/4, 124, 133, 137; 358/113; 348/164, 165, 166, 167, 168

[56] References Cited

U.S. PATENT DOCUMENTS

| | | | |
|---|---|---|---|
| 3,531,642 | 9/1970 | Barnes et al. | |
| 3,854,336 | 12/1974 | Bibby | 73/351 |
| 4,379,461 | 4/1983 | Nilsson et al. | 128/736 |
| 4,524,386 | 6/1985 | Scott | 348/164 |
| 4,539,588 | 9/1985 | Ariessohn et al. | |
| 4,671,674 | 6/1987 | Detronde | 374/5 |
| 4,687,344 | 8/1987 | Lillquist | 250/332 X |
| 4,695,881 | 9/1987 | Kennedy et al. | |
| 4,733,079 | 3/1988 | Adams et al. | 250/341 |
| 4,814,870 | 3/1989 | Crall | 348/168 |
| 4,849,885 | 7/1989 | Stillwagon et al. | 364/413.1 |
| 4,854,724 | 8/1989 | Adams et al. | 374/5 |
| 4,910,593 | 3/1990 | Weil | 348/164 |
| 5,045,937 | 9/1991 | Myrick | 348/164 X |
| 5,292,195 | 3/1994 | Crisman, Jr. | 250/330 X |

FOREIGN PATENT DOCUMENTS

| | | | |
|---|---|---|---|
| 59-115686 | 7/1984 | Japan | 358/113 |
| 63-175735 | 7/1988 | Japan | 250/330 |

OTHER PUBLICATIONS

Cross et al., "Measurement of Aircraft Surface Temperatures with an Infrared Television System", Proceedings of SPIE 14th Annual Technical Symposium: Photo-Optical Inst. App. & Theory, San Francisco, Calif., Aug. 1969, pp. 59–65.
Freund, "Infrared Scanning Added to Routine Maintenance", Exergen Corp., EC&M, Oct. 1987, pp. 67–70.
Mikron Advertisement, Oct. 1990.
Sales Brochure—Thermovision 470 by Agema.
Sales Brochure—700 Series by Inframetrics.

*Primary Examiner*—Constantine Hannaher
*Assistant Examiner*—Edward J. Glick
*Attorney, Agent, or Firm*—Luedeka, Neely & Graham

[57] ABSTRACT

A system including a mobile infrared thermography unit and a base station for automating the collection of thermographic data and for facilitating the efficient generation of reports. The mobile infrared thermography unit includes an infrared camera, a storage device such as a videotape recorder for at least recording thermographic images captured by the infrared camera, and a mobile unit computer. The mobile unit computer includes a touch screen display for presenting information to a thermographer and for receiving data and command inputs from the thermographer. The mobile unit computer is interfaced to the infrared camera or the videotape recorder for maintaining a record, either by tape position or date/time stamp, where thermographic images of particular equipment are recorded. The mobile unit computer includes a display operable to prompt the thermographer with route information regarding particular equipment to be thermographically inspected, as well as to suggest to the thermographer particular problems possibly indicated by a particular thermographically-observed condition. The base station includes a base station computer which transfers information to the mobile unit computer prior to undertaking an inspection route, and receives information from the mobile unit computer when the route is completed. The base station computer is capable of directly accessing and downloading particular infrared images recorded by the videotape recorder, employing the tape position or date/time stamp information.

26 Claims, 11 Drawing Sheets

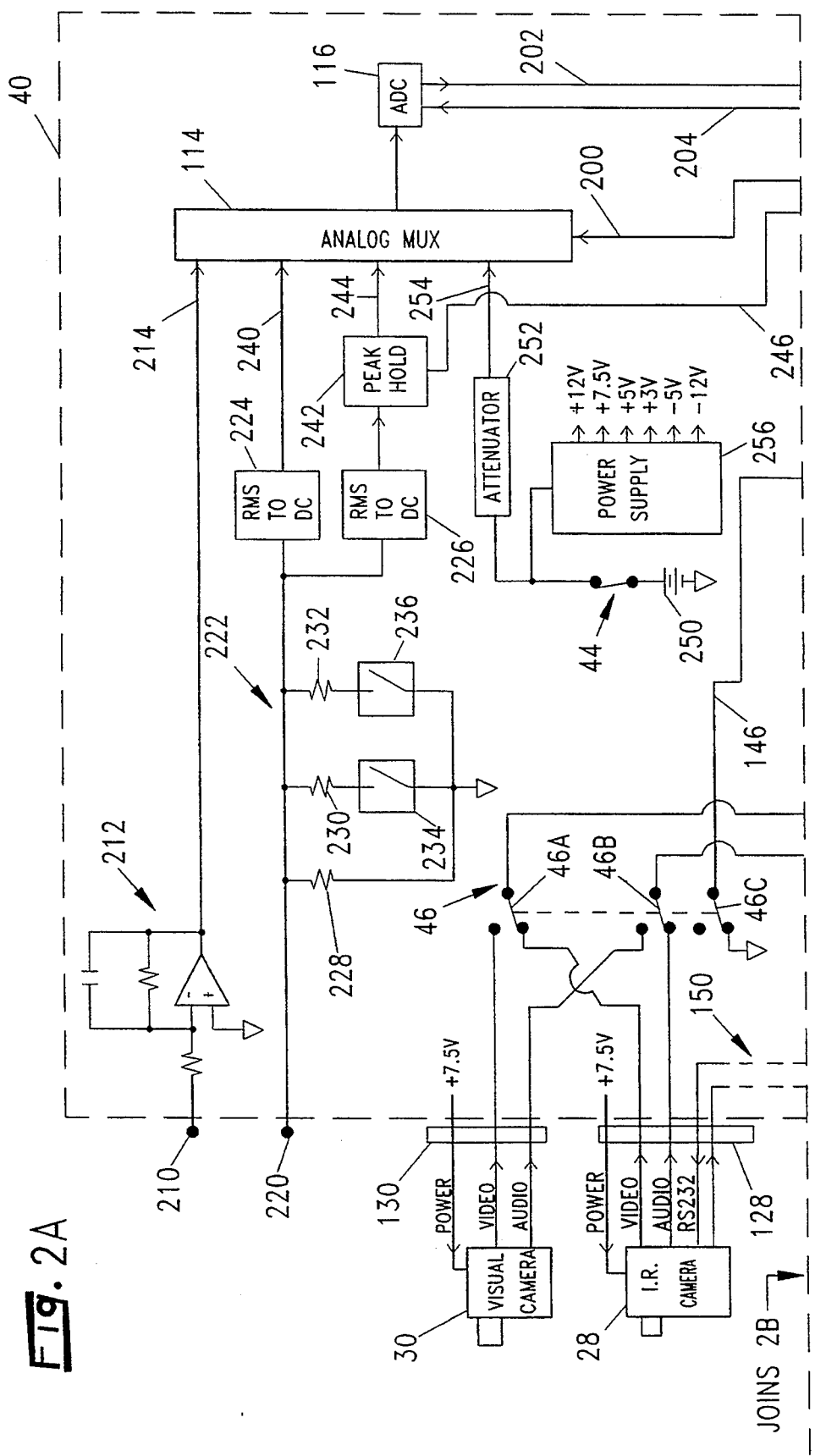

| MAIN | Identify Location of Fault |
|---|---|
| BACKUP | |
| POINT LIST | Control cabinet  1 0 0 0 - A |
| HELP | Elevation  2nd Floor |
| Un Do | Grid X  1 2 5 ⎯ Feet |
| Accept | Grid Y  5 2 ⎯ Feet |

Fig. 6

| MAIN | Identify Faulty Componet |
|---|---|
| BACKUP | Motor Control Center Components |
| POINT LIST | Breaker |
|  | Buss Bar |
| HELP | Conduit |
|  | Fuse |
| ACCEPT | Fuse Clip |

Fig. 7

| MAIN | Identify Fault Type |
|---|---|
| BACKUP | Fuse Fault Types |
| POINT LIST | Discoloration |
|  | Fuse-fatigued |
| HELP | Fuse-improper size or load |
|  | Fuse-mismatched size or rating |
| ACCEPT | Hot spot |

| | | Fuse-fatigued Recommended Actions |
|---|---|---|
| MAIN | [X] | Report to electrical superviser |
| BACKUP | [X] | Take amperage readings |
| Point List | [X] | Check for grounds |
| HELP | [X] | Check for proper ground |
| All Actions | [X] | Clean |
| Accept | [ ] | |

Fig. 10

| | | All Defined Recommended Actions |
|---|---|---|
| MAIN | [X] | Check for grounds |
| | [ ] | Check for leaks |
| All Off | [X] | Check for proper ground |
| HELP | [ ] | Check for wear |
| Un Do | [ ] | Check line up |
| Accept | [ ] | Check Load |
| | [ ] | Check oil level |

Fig. 11

Record Temperature and Emissivity

- MAIN
- BACKUP
- Point List
- HELP
- Measure
- Accept

Exception Temp: 130.0
Reference Temp: 110.0
Background Temp: 70.0
Ambient Temp: 70.0
Estimated Emissivity: 0.950

Fig.12

Record Electrical and Outdoor Data

| Circuit Phase | Actual Load | Rated Load | Voltage |
|---|---|---|---|
| ○ A ● B ○ C | 1 0 0 | 1 2 0 | 4 4 0 |

| Componet In Didect Sunlight | Wind Speed | Wind Direction |
|---|---|---|
| ☐ | 6 | W |

Fig.13

Record Image Parameters

| Thermal Image Location | Visual Image Location |
|---|---|
| 1 : 1 5 : 2 0 | 1 : 1 6 : 4 7 |

| Aperature | Filter | Lens |
|---|---|---|
| 3 . 1 | 0 . 0 0 0 | 2 5 . 0 |

Fig.14

Severty of Fault Condition

| Calculated Temperature Rise 20.0 F | Estimated Priority = Intermediate |
|---|---|
| | Assigned Priority = Intermediate |
| Percent Full Load 83.3 % | Repair within 2-4 weeks. Inspect for physical damage Watch for load changes Chance of component damage |

```
┌─────────┬──────────────────────────────────────────┐
│ (MAIN)  │      Select Equipment Category           │
│(BACKUP) │   ┌───────────┐    ┌──────────────────┐  │
│         │   │ Electrical│    │ Mechanical-Static│  │
│ (HELP)  │   └───────────┘    └──────────────────┘  │
│         │   ┌───────────┐ ↖  ┌──────────────────┐  │
│         │   │ Switchyard│    │    Structural    │  │
│         │   └───────────┘    └──────────────────┘  │
│         │ ┌──────────────────┐ ┌────────────────┐  │
│         │ │Mechanical-Dynamic│ │ Miscellaneous  │  │
│         │ └──────────────────┘ └────────────────┘  │
└─────────┴──────────────────────────────────────────┘
```

Fig.15

```
┌─────────┬──────────────────────────────────────────┐
│ (MAIN)  │         Select Equipment Type            │
│(BACKUP) │  ┌────────────────────────────────────┐  │
│         │  │    Switchyard Equipment Types      │  │
│         │  │ Motor Operated Switch              │  │
│ (HELP)  │  │ Insulator                          │  │
│         │  │ Manual Disconnect Switch           │  │
│         │  │▓Ground Switch▓▓▓▓▓▓▓▓▓▓▓▓▓▓▓▓▓▓▓▓▓▓│  │
│(ACCEPT) │  │ Main Transformer        ↖          │  │
│         │  └────────────────────────────────────┘  │
└─────────┴──────────────────────────────────────────┘
```

Fig.16

```
┌──────────┬─────────────────────────────────────────┐
│ (Main)   │      Name the Specific Equipment        │
│(Backup)  │       Switchyard-Ground Switch          │
│(Pointlist)│         Equipment Description          │
│          │     N O R T H  Y A R D  S W I T C H  1 7│
│ (HELP)   │                                         │
│          │  ┌────────────────────────┐ ┌─────────┐ │
│          │  │Equipment ID  switch 17 │ │Equip    │ │
│ (Accept) │  └────────────────────────┘ │Indoors □│ │
│          │                             └─────────┘ │
└──────────┴─────────────────────────────────────────┘
```

| COMPONENT | SUB COMPONENT | FAULT | LOOK FOR | RECOMMEND | REPORT |
|---|---|---|---|---|---|
| TRANSFORMER CONTROL CUBICAL (VISUAL) | FUSES | IMPROPER SIZE FOR LOAD | MISMATCHED FUSE SIZE OR RATING | REPLACEMENT OF MISMATCHED FUSE | ANY TIME A THERMAL ANOMALY IS FOUND |
| | FUSE CLIPS | LOOSE SCREWS | UNEVEN THERMAL PROFILE BETWEEN CONNECTIONS | REPAIR, REPLACE, REWORK | WHEN EXCEEDING THERMAL LIMITS |
| | | WEAK CLIPS | TOP BOTTOM OR SIDE OF CLIP IS HOT | REPLACEMT OF CLIP | ALL FINDINGS, CLIPS ONLY GET WORSE |
| | BREAKERS | | IS THE BREAKER OF PROPER SIZE FOR LOAD | REPLACEMENT IF UNDER SIZE | WHEN FOUND |
| | | BODY IS EXCEEDING THERMAL LIMITS | ARE THE FITTING TIGHT | REWORK CONNECTIONS | WHEN EXCEEDING THERMAL LIMITS |
| | | | PHASE IMBALANCE | ELECTRICAL DEPARTMENT INVESTIGATE | EVERY INSTANCE FOUND |
| | WIRE CONNECTIONS | CONNECTION END OF WIRE IS HOT | IMPROPER CRIMP OR UNDER SIZE FITTING | REWORK | EVERY INSTANCE FOUND |
| | | CANDY STRIPING | BROKEN STRAND OR KINK IN WIRE BODY | REPLACE WIRE | DEGREE OF THERMAL IMBALANCE AND LOCATION |
| | | ENTIRE WIRE IS HOT | PHASE IMBALANCE | ELECTRICAL CHECK | EVERY INSTANCE FOUND |
| | CONDUIT | HOT SPOT | PHASE IMBALANCE GROUND | TAKE AMPERAGE READING CHECK FOR CAUSE | LOCATION AND EXTENT EVERY INSTANCE FOUND |
| (INFRARED) | RAYCHEM | MELTING | SHORTS OR WATER INTRUSION | SHUTDOWN AND IMMEDIATE REPAIR | EXACT LOCATION AND EXTENT OF DAMAGE |

| COMPONENT | | SUB COMPONENT | FAULT | LOOK FOR | RECOMMEND | REPORT |
|---|---|---|---|---|---|---|
| MCC CABINET | VISUAL | FUSES | FUSE IS FATIGUED | EXTERNAL DAMAGE | REPLACE | ANY ANOMALY |
| | | FUSES | IMPROPER SIZE OR TYPE FOR LOAD | MISMATCHED FUSE SIZE OR RATIN OR MANUFACTURE | REPLACEMENT OF MISMATCHED FUSE | ANY TIME A THERMAL ANOMALY IS FOUND |
| | | FUSE CLIPS | LOOSE SCREWS | UNEVEN THERMAL PROFILE BETWEEN CONNECTIONS | REPAIR, REPLACE, REWORK | WHEN EXCEEDING THERMAL LIMITS |
| | | FUSE CLIPS | WEAK CLIPS | TOP BOTTOM OR SIDE OF CLIP IS HOT | REPLACEMT OF CLIP | ALL FINDINGS, CLIPS ONLY GET WORSE |
| | | BREAKERS/SWITCH | | IS THE BREAKER OF PROPER SIZE FOR LOAD | REPLACEMENT IF UNDER SIZE | WHEN FOUND |
| | | BREAKERS/SWITCH | BODY IS EXCEEDING THERMAL LIMITS | ARE THE FITTING TIGHT | REWORK CONNECTIONS | WHEN EXCEEDING THERMAL LIMITS |
| | | BREAKERS/SWITCH | | PHASE IMBALANCE | ELECTRICAL DEPARTMENT INVESTIGATE | EVERY INSTANCE FOUND |
| | | WIRE CONNECTIONS | CONNECTION END OF WIRE IS HOT | IMPROPER CRIMP OR UNDER SIZE FITTING | REWORK | EVERY INSTANCE FOUND |
| | | WIRE CONNECTIONS | CANDY STRIPING | BROKEN STRAND OR KINK IN WIRE BODY | REPLACE WIRE | DEGREE OF THERMAL IMBALANCE AND LOCATION |
| | | WIRE CONNECTIONS | ENTIRE WIRE IS HOT | PHASE IMBALANCE | ELECTRICAL CHECK | EVERY INSTANCE FOUND |
| | | CONDUIT | HOT SPOT | PHASE IMBALANCE | TAKE AMPERAGE READING | LOCATION AND EXTENT |
| | | CONDUIT | | GROUND | CHECK FOR CAUSE | EVERY INSTANCE FOUND |
| | | BUSS BAR | HOT SPOT | ENSURE FIXTURES ARE MADE UP PROPERLY | PROPER TORQUE OF FIXTURE AND COMPONENTS | EXACT LOCATION AND EXTENT OF DAMAGE |
| | INFRARED | HEATER/OVERLOADS | BURNED | VISABLE DAMAGE | REPLACEMENT | EVERY INSTANCE FOUND |

INFRARED THERMOGRAPHY SYSTEM INCLUDING MOBILE UNIT

BACKGROUND OF THE INVENTION

The present invention relates generally to the art of infrared thermography and, more particularly, to a system which facilitates the collection of data by a thermographer, the efficient preparation of reports, and the archiving of records relating to thermographic inspection. The invention further relates to automating the process of field data collection, for complete and efficient documentation of thermographic events.

Infrared thermography, whereby infrared cameras are employed to acquire infrared images at any one of several infrared wavelength ranges, is known to be useful in a wide variety of applications. An observed anomaly or problem is known as a thermographic "event" to be reported and possibly diagnosed. The invention is disclosed herein in the context of industrial plant maintenance, also known as preventative maintenance or predictive maintenance. However, by way of example, and not limitation, infrared thermography is useful in a variety of applications other than plant maintenance, such as EPA studies, agriculture, medical technology, law enforcement, veterinary medicine and military uses.

As one example of a plant maintenance application, an infrared image of the interior of a three phase electric motor switch box may reveal that one fuse out of three, or the fuse connectors, is hotter than the other two, indicating a potential problem to be corrected before an actual failure occurs.

As another example, within a three phase electrical control box, a conductor associated with one of the phases may be colder than corresponding conductors associated with the other two phases, indicating that less current is being carried, and pointing to a potential problem to be investigated.

As other examples, within the exemplary context of industrial plant maintenance, the following components may advantageously be inspected employing infrared thermography: transformers, transformer control cubicles, motor control centers, transmission lines, electric motors, steam traps, pipes, valves, belts, components subject to vacuum leaks, insulation in general, roofs and roof insulation, dry type transformers, rotary kilns, auxiliary transformers, start up transformers, distribution panel circuit breakers, relays and ground straps.

Prior art infrared thermography systems have been labor intensive and relatively inefficient from the viewpoint of enabling a thermographer to rapidly and efficiently generate reports. Moreover, prior art thermography systems rely a great deal upon the skill and experience of the thermographer, and it may take two or three years for a thermographer to become well qualified.

In the context of the present invention, it may be noted that there are known prior art thermography systems which employ infrared cameras connected to a videotape recorder whereby a thermographer can record infrared images of various pieces of equipment and other things for later review. Later, when the thermographer is preparing a report, the videotape is played until desired images are found, which are displayed on a screen, and then captured for a permanent record, either photographically off of the video screen, or digitally.

Another prior art approach to thermography employs an infrared camera having what is in effect "snapshot" capability whereby a limited number of thermographic images, for example thirty three images, may be digitally captured to a floppy disk included within the infrared camera, for later review.

In prior art thermography systems, visible images are typically also captured, either employing a separate visible image video camera or a conventional photographic snapshot camera. While images are being captured, the thermographer makes notes of various observations as necessary to facilitate later preparation of a report.

These prior art approaches are highly labor intensive, particularly when reports are being prepared. It is not unusual for each hour a thermographer spends in the field to result in one or two days of time spent reducing data and preparing reports. Typically, while generating reports, the thermographer spends many hours looking through videotape images looking for particular thermographic events to document.

In the context of the present invention, it is also pertinent to note that there are prior art systems which employ computers to aid the thermographer. Typically, these computers are employed as a data analysis tool, such as to manipulate thermographic images for identifying specific values, average temperature over some area, isotherms, or line temperature profiles, rather than for purposes of documentation.

SUMMARY OF THE INVENTION

Accordingly, it is an object of the invention to provide apparatus for automating the collection of thermographic data, and for greatly reducing the time required for a thermographer to produce a report.

It is another object of the invention to provide apparatus for infrared thermography which facilitates the complete documentation of thermographic events.

It is yet another object of the invention to provide a thermographic system which assists a thermographer, whether an experienced thermographer or a relatively inexperienced thermographer, in following a predetermined route when conducting thermographic inspections, and in inspecting particular points of equipment and things on that route.

It is yet another object of the invention to provide a thermographic system which aids in the diagnosis of particular faults in the manner of an "expert" system, and which prompts a thermographer regarding the manner in which particular problems are to be reported.

It is yet another object of the invention to provide a thermographic inspection system which automatically provides well documented "proof" of inspection, with date and time logging.

Briefly, in accordance with one aspect of the invention there is provided a mobile infrared thermography unit including an infrared camera and a storage device, such as a videotape recorder or digital storage device, for at least recording thermographic images captured by the infrared camera. The mobile infrared thermography unit additionally includes a data processing device which performs a variety of functions. The data processing device is interfaced to at least one of the infrared camera and the storage device for at least maintaining a record of identifying information related to recorded thermographic images. The identifying information may comprise an indication of where thermographic images of particular equipment are recorded in the storage device, for example, a videotape position indication, a time and date stamp, or a specific frame/record of a digital storage device. In any event, a particular thermographic image can subsequently be automatically found on the videotape for retrieval without having to manually scan through a lengthy videotape recording, for example, to find the particular image.

The mobile infrared thermography unit additionally includes a visible image camera and a switch for selectively connecting either the infrared camera or the visible image camera to the storage device for image recording. Preferably, the data processing device is interfaced to the switch for acquiring data relating to which camera, visible or infrared, has produced a particular recorded video image, and maintaining a record.

The mobile infrared thermography unit additionally includes a microphone connected to the storage device such that a thermographer's comments relating to a particular thermographic or visible image may be recorded with the image to aid in subsequent report generation.

In accordance with another aspect of the invention, the mobile unit data processing device includes a display, and is operable to prompt a thermographer regarding particular equipment to be thermographically inspected. In other words, a route to be followed by the thermographer may be loaded into the data processing device. In an "on route" situation, all route information is preloaded into the data processing device, along with instructions regarding how equipment is to be thermographically scanned in special circumstances. In an "off route" situation, the thermographer is provided with the capability of defining machines and thermographic events in the field.

The mobile unit data processing device preferably is also operable to suggest to the thermographer particular problems possibly indicated by a particular thermographically-observed condition, typically presented in a hierarchical menu display, somewhat in the manner of an "expert" system. Thus, a relatively inexperienced thermographer is enabled to efficiently produce useful reports.

Preferably, the mobile infrared thermographic unit also includes at least one interface between the mobile unit data processing device and an external measurement instrument, such as a temperature measurement device or a current measurement device. In addition, the mobile infrared unit itself includes an RMS AC current measurement interface and a voltage measurement interface to the mobile unit data processing device.

In accordance with another aspect of the invention, an infrared thermography system includes a mobile infrared thermography unit as briefly summarized above and, in addition, a base station to which the mobile unit is connected at the beginning and end of field thermographic data collection. The base station includes a base station data processing device operable, when the mobile thermographic unit is connected to the base station, to download identifying information from the mobile unit data processing device, as well as to download recorded thermographic images from the mobile unit storage device. To this end, the base station data processing device, when connected, controls the videotape recorder to locate specific frames by the date/time stamp, and includes a video frame grabber for transferring thermographic images to the base station data processing device. Alternatively, in the event images are stored in digital form in the mobile unit, digital images are downloaded directly, without the use of a video frame grabber. In any event, thermographic images are stored in the base station data processing device in digital form.

The base station data processing device is further operable, when the mobile thermographic unit is connected to the base station, to upload user prompting information to the mobile unit data processing device.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description, taken in conjunction with the drawings, in which:

FIGS. 2A and 2B, when joined, are an electrical schematic diagram depicting a power distribution and control box included as part of the FIG. 1 mobile thermographic unit, several other devices included in the FIG. 1 mobile thermographic unit, and elements of the base station including the data processing device;

FIGS. 6, 7 and 8 are examples of fault documentation screens which may be presented on the display of the mobile unit data processing device;

FIGS. 9 and 10 are examples of a recommended action screen which may be presented on the display of the mobile thermographic unit;

FIGS. 11, 12, 13 and 14 are examples of screens which may be presented on the display of the mobile unit data processing device to aid in recording information relating to a fault;

FIGS. 15, 16, 17 and 18 are examples of screens which may be presented on the display of the remote unit data processing device to enable a thermographer to establish an item of "off route" equipment;

FIG. 19 is an example of an infrared fault flowchart for a transformer control cubicle which may be embodied in a pyroelectric series of screens in the manner of an "expert" system to aid a thermographer in diagnosing a fault; and FIG. 20 is a similar example of an infrared fault flowchart for a motor control center cabinet.

DETAILED DESCRIPTION

Figure 1:
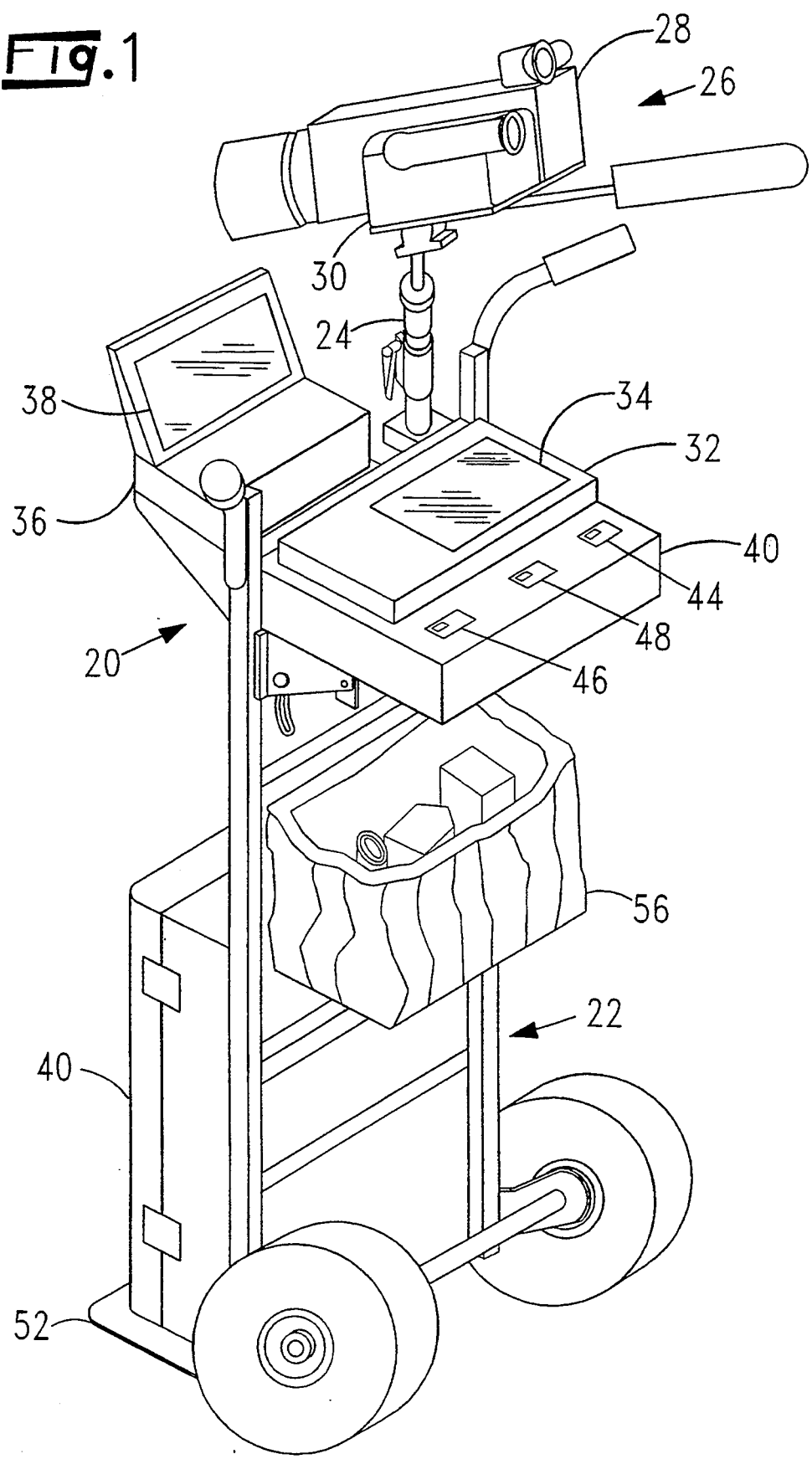
FIG. 1 depicts a mobile infrared thermography unit in accordance with the invention.

FIG. 1 is a three dimensional view of a mobile infrared thermography unit 20 embodying the invention. The infrared thermography unit 20 is constructed on a suitable base, which may comprise an ordinary hand truck 22. Suitably mounted to the base 22 by means of a mount 24 is a camera assembly, generally designated 26, including an infrared camera 28 and an ordinary visible image camera 30.

Any suitable infrared camera 28 may be employed in the practice of the invention including, by way of example and not limitation, pyroelectric infrared cameras and focal plane array cameras which may include platinum silicide detectors. A typical pyroelectric infrared camera has the characteristics of longwave imaging (8 to 12 micrometers) and good image resolution, with no detector cooling required. A typical focal plane array camera employing a platinum silicide detector has the characteristics of shortwave imaging (2.5 to 5 micrometers) and extremely high image resolution, and includes a built-in battery powered detector cooler. Particular commercially-available infrared cameras which are suitable are the "Pyroviewer" infrared camera and the "Flir" infrared camera.

Likewise, any suitable visible image camera 30 may be employed. So-called "camcorders" combining a video camera and a video tape recorder are more readily available than are video cameras alone, and it is accordingly advantageous to simply employ the camera portion of a camcorder, while bypassing the recorder portion thereof. One which has been found to be suitable is a Sony "Handycam" camcorder.

Also included is a mobile unit data processing device 32, which preferably is an IBM PC compatible computer including an Intel 8088-compatible processor, internal memory, and an internal hard disk drive. Presently preferred is a pen-based computer 32 which includes a combined LCD display and touch screen type pen digitizer 34 (and corresponding handwriting-recognition software), rather than a conventional keyboard. A suitable pen-based computer 32 which may be employed as the remote unit data processing device 32 is a "Poquet Pen Plus" available from Fujitsu Personal Systems, Inc., 5200 Patrick Henry Drive, Santa Clara, Calif. 95054. The "Poquet Pen Plus" pen-based computer combines a 640×200 resolution LCD display with a 200 points/inch resolution pen digitizer, with an MS-DOS operating system and built-in handwriting-recognition software.

For recording both infrared and visible images produced by the cameras 28 and 30, a videotape recorder 36 is provided, preferably also incorporating a monitor screen 38. Presently preferred is a Sony "Walkman" Model No. GV-S50 NTSC Video Recorder/Monitor 36. This particular video recorder/monitor includes a 4 inch×4 inch fold-out color LCD display, and employs "Hi-8 mm" format videotape, with a separate track for recording data and time stamps corresponding to images being recorded. The Sony "GV-S50" video recorder/monitor 36 is an intelligent device, and has a bi-directional control interface 39 (FIG. 2B) implementing LANC technology as documented by Sony.

One alternative to the videotape recorder 36, is a digital image storage device wherein images are accessed, for example, by frame or record. The digital storage device may comprise an element of the computer 32.

A power distribution and control box 40 functionally interconnects the infrared and video cameras 28 and 30, the mobile unit data processing device 32 and the videotape recorder 36, and additionally supplies power to these components. Circuitry within the power distribution and control device 40 is described hereinbelow with reference to FIGS. 2A and 2B. However, at this point it may be noted that the power distribution and control box 40 is an intelligent device including a microprocessor or microcontroller 42 (FIG. 2B) which performs functions under the control of the mobile unit data processing device 32. The power distribution and control box 40 has at least three switches 44, 46 and 48 operable by the thermographer. Briefly, the switch 44 is a power switch. The switch 46 selects either the infrared 28 or video 30 camera for image recording by the videotape recorder 36. The switch 48 is an audio selector switch 48 for selecting a source of audio to be recorded by the videotape recorder 36 along with images.

The power distribution and control box 40, as its name implies, additionally serves the function of distributing power to the remainder of the equipment. Preferably, the main source of power is a battery which may either be included within the power distribution and control box 40 or, preferably, is supported on a lower support plate 52 of the hand truck 22.

The mobile unit 20 additionally includes a utility pouch 56 for convenient storage of a variety of items useful to a thermographer, such as, but not limited to, portable instruments for measuring the temperature of a particular point on a piece of equipment, instruments for determining and compensating for emissivity of objects being viewed with the infrared camera 28, remote current-measuring probes, remote temperature-measuring probes and other remote measurement devices.

Although not shown in FIG. 1, it will be appreciated that there are various cables for interconnecting the components as required. In addition, the power distribution and control box 40 preferably includes capabilities for directly measuring RMS current and DC volts. Particularly when acquiring thermographic images of electrical equipment, proper analysis and documentation requires measurement and recording of a variety of conditions, for example, ambient temperature, and current flow through particular circuits.

Figure 2B:
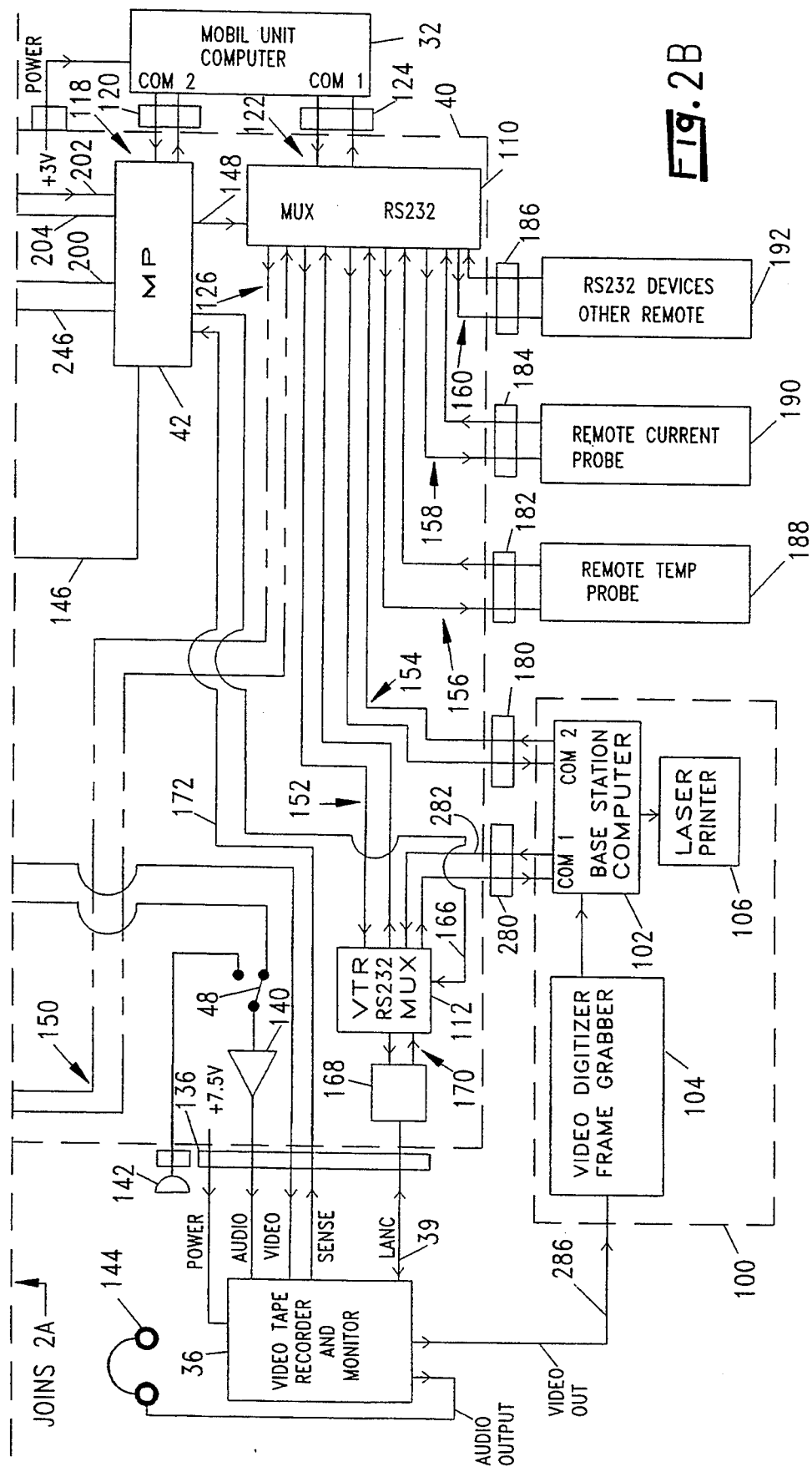

FIGS. 2A and 2B, when joined, are a somewhat simplified electrical schematic diagram of internal elements within the power distribution and control box 40 and, in addition, connections to the infrared camera 28, the visual camera 30, the mobile unit data processing device 32 (the "Poquet Pen Plus" computer), and the videotape recorder and monitor 36. In accordance with the invention, the mobile unit 20 is selectively connected to a base station, generally designated 100, including a base station computer 102 comprising another IBM-PC compatible computer, preferably of the 80386 or 80486 class, with at least a 200 megabyte hard drive and a color VGA monitor. Connected to the base station computer 102 is a digitizer/frame grabber 104 which, it will be appreciated, is typically included within the same physical case as the base station computer 102. For producing documentation, including digitized images, a laser printer 106 is connected to the base station computer 102. The mobile unit 20 is typically connected to the base station 100 at the beginning and end of thermographic data collection in the field.

Considering circuitry within the power distribution and control box 40 in greater detail, the microprocessor or microcontroller 42 serves the straightforward and primary function of controlling several multiplexers, including an RS232 multiplexer 110, a videotape recorder RS232 multiplexer 112, and an analog multiplexer 114, and additionally controls an analog-to-digital converter 116, all generally in response to commands received from the mobile unit data processing device 32 (i.e. the "Poquet Pen Plus" computer).

To this end, the microprocessor or microcontroller 42 includes a port 118 programmed for bi-directional RS232 communication and connected through a connector 120 to the "COM2" port, for example, of the mobile unit computer 32. The "COM1" port of the mobile unit computer 32 is connected to the common port 122 of the multiplexer 110 through a connector 124. Thus, the "COM1" port is in effect selectively connected through the RS232 multiplexer 110 to any one of a plurality of multiplexed ports 126 under control of the microprocessor or microcontroller 42, which is in turn directed by the mobile unit computer 32 through its "COM2" port. In this particular configuration, the "COM1" port of the mobile unit computer 32 may be termed a communications port, and the "COM2" port may be termed a command port.

Although the RS232 multiplexers 110 and 112 are each shown as a single device, in practice this implied functionality is preferably achieved employing separate multiplexers (not shown) for transmit data and for receive data, both operating under control of the microprocessor 42. Further, the separate multiplexers themselves may comprise TTL devices, with separate conventional interface devices (likewise not shown) for level conversion between RS232 and TTL voltage levels as required, all in accordance with conventional practice. In any event, the RS232 multiplexer 110 thus serves to selectively connect any one of several RS232 data links on the multiplexed port 126 side to the "COM1" or communications port of the mobile unit computer 32 on the common port 122 side of the multiplexer 110. Each of the RS232 data links comprises a pair of lines, conventionally respectively termed "transmit data" and "receive data", Although omitted for clarity of illustration, it will be appreciated that there is also a data ground or common connector. Some RS232 devices require other control lines, as is well known.

The infrared and visual cameras 28 and 30 are connected to the power distribution and control box 40 through suitable cables and respective connectors 128 and 130, and the videotape recorder and monitor 36 is connected to the power distribution and control box 40 through a suitable cable and a connector 136.

The user-operable switch 46 has three poles 46a, 46b and 46c, and functions primarily as a video source selection switch. Pole 46a of the video source selection switch 46 thus serves to selectively connect video output from either the infrared camera 28 or the visual camera 30 to a video input of the videotape recorder and monitor 36. In the switch 46 position shown, video signals from the infrared camera 28 are connected to the videotape recorder 36. When thrown to the opposite position, video signals from the visual camera 30 are connected to the video input of the videotape recorder 36 through the switch pole 46a.

In addition, the switch pole 46b serves to selectively connect audio from either the infrared camera 28 or the visual camera 38, through the audio selector switch 48 and an audio amplifier 140 to an audio input of the videotape recorder and monitor 36. A volume control (not shown) may be associated with the audio amplifier 140. For situations where a particular camera does not include a microphone, or when it is simply desired to use a separate microphone, a separate microphone 142 is provided and selectively connected through the audio selector switch 48 and the audio amplifier 140 to the videotape recorder 36 audio input. The microphone 142 may comprise either a lapel microphone, or an element of a headset/microphone. For monitoring audio being recorded, thus ensuring that audio is in fact being recorded, the headset 144 of the headset/microphone is connected to the audio output of the videotape recorder and monitor 36.

To enable microprocessor monitoring of the position of the video source selection switch 46, a third switch pole 46c is connected to selectively ground a sense line 146 connected to the microprocessor 42. Although not shown in the drawing, typically a pull-up resistor is connected between the sense line 146 and a source of +5 volts DC.

The multiplexing feature whereby the "COM1" communications port of the mobile unit computer 32 is selectively connected to a variety of RS232 devices will now be considered in greater detail.

The RS232 multiplexer 110, under control of the microprocessor or microcontroller 42 as indicated by a control line 148, selectively connects the RS232 multiplexer 110 common port 122 to any one of a plurality of RS232 data links 150, 152, 154, 156, 158 and 160 connected to the RS232 multiplexer multiplexed ports 126. Operations of the microprocessor or microcontroller 42 are in turn directed by the portable unit computer 32 through its "COM2" port.

The data link 150 is optional, depending upon the particular infrared camera 28 employed, and thus is shown in phantom lines. Some infrared cameras 28, such as the "Flir", include an RS232 communications port to facilitate data communications with the camera.

For communicating with the Sony "GV-S50" video recorder monitor 36 via its LANC interface 39, the data link 152 is connected through the videotape recorder RS232 multiplexer 112 (which is controlled by the microprocessor 42 via a control line 166) and through an interface circuit 168 which interfaces between the bi-directional LANC interface 39 and a pair of individual transmit and receive data lines 170 connected to the common port of the videotape recorder RS232 multiplexer 112. The data lines 170 may operate at TTL or RS232 voltage levels, depending on the particular interface and multiplexing circuitry employed. By means of the data link 152, the mobile unit computer 32 thus effects control over the videotape recorder and monitor 36.

Additionally, a representative sense line 172 is provided, which actually represents individual sense lines connected to the "record" and "record stop" switches within the videotape recorder 36, such that the microprocessor 42 is able to sense the operational condition of the "record" and "record stop" switches.

The RS232 data link 154 from the multiplexer 110 is selectively connectable through a connector 180 to the base station 100 and, more particularly, to representative "COM2" port of the base station computer 102 to selectively permit data communication between the base station computer 102 and the mobile unit computer 32, in a manner described in greater detail hereinbelow.

In certain thermography situations, it is desirable and even necessary to acquire data in addition to video and infrared images. More particularly, it is typically relevant to acquire other data such as spot temperature, motor current, emissivity, background radiation, and the like for purposes of analysis and for inclusion in reports.

Thus, RS232 data links 156, 158 and 160 from the RS232 multiplexer 110 are selectively connectable through connectors 182, 184 and 186 to respective remote instruments including, by way of example, a remote temperature probe 188, a remote current probe 190, and other remote RS232 devices generally designated 192. Accordingly, the mobile unit computer 32 can directly acquire data from the instruments 188, 190 and 192 for analysis and for inclusion in reports. The remote instruments 188, 190 and 192 are advantageously stored in the FIG. 1 utility pouch 56 when not in use.

In addition to connection to the remote instruments 188, 190 and 192, which are RS232 devices, the power distribution and control box 40 itself includes current and voltage measurement capability, effected by means of the analog multiplexer 114 and the analog-to-digital converter 116 through which the microprocessor 42 acquires further analog data. The analog multiplexer 114 is controlled by the microprocessor 42 by means of a control line 200. The microprocessor 42 receives digital data from the analog digital converter 116 and controls the operation thereof through lines 202 and 204, in a conventional manner.

More particularly, for voltage measurements, a DC voltmeter input terminal 210 is connected through an operational amplifier signal conditioning circuit 212, having appropriate integration and gain constants, to a first input 214 of the analog multiplexer 114.

For measurement of current, a current input terminal 220 is connected to a controllable shunt resistor circuit 222 across which a voltage is developed depending on current in accordance with Ohm's Law, which voltage is supplied to a pair of RMS to DC converters 224 and 226. The controllable shunt register circuit 222 includes three shunt resistors 228, 230 and 232 and two latching relay contacts 234 and 236 which together serve to selectively establish full scale readings of fifty, five hundred and five thousand RMS AC amperes. The latching relay contacts 234 and 236 are under the control of the microprocessor or microcontroller 42 through suitable control lines and interface circuitry (not shown).

The two RMS to DC converters 224 and 226 have different time constants and the output of one or the other is selected for use depending upon the particular measurement situation.

The output of the RMS to DC converter 224 is connected directly to a second input 240 of the analog multiplexer 114. The output of the RMS to DC converter 226 is connected to a peak hold circuit 242, the output of which is in turn connected to a third input 244 of the analog multiplexer 114. As is known, a peak hold circuit 242 typically comprises a capacitor (not shown) which temporarily holds a peak voltage, the capacitor being connected to the input of a high input impedance amplifier (not shown) through which the capacitor voltage is sensed. A reset circuit (not shown) is also provided for discharging the capacitor prior to another reading. A reset line 246 from the microprocessor 42 controls resetting of the peak hold circuit 242.

Power for the power distribution and control box 40, as well as various other devices on the mobile unit 20, is supplied by a battery 250, such as a twelve-volt battery. The battery 250 may be internal to the power distribution in control box 40, but preferably is external, typically secured to the lower plate 52 of the FIG. 1 hand truck 22. The battery 250 is connected to the circuitry through the power switch 44.

To enable monitoring of the battery 250 voltage, the power switch 44 output is connected through an attenuator 252 to a fourth input 254 of the analog multiplexer 114. The battery voltage attenuator 252 may comprise an operational amplifier signal conditioning circuit, similar to the circuit 212, and configured for less than unity gain.

A power supply circuit 256 is supplied by the battery 250 through the power switch 44, and supplies various operating voltages as indicated for the power distribution in control box 40. Appropriate operating voltages are additionally supplied to various external devices such as the infrared camera 28, the visual camera 30 and the videotape recorder and monitor 36 as indicated, as well as the mobile unit computer 32.

When the mobile unit 20 is not in the field gathering data, it is at times connected to the base station 100, and, more particularly, to the base station computer 102 for data transfer between the base station computer 102 and the mobile unit computer 32 via the RS232 data link 154. In addition, through a connector 280 and an RS232 data link 282, the "COM1" port of the base station computer 102 communicates through the multiplexer 112 to the LANC control interface 39 of the videotape recorder the monitor 36.

In addition, video output from the videotape recorder 36 is connected via a line 286 to the digitizer/frame grabber 104, which is in turn connected to or comprises a part of the base station computer 102. Typically, the digitizer/frame grabber 104 is a high resolution real-time color video frame grabber, which comprises a full-size 16-bit card within the base station computer 102, supporting both NTSC and PAL video input signals. To facilitate the subsequent and efficient generation of reports including images on the laser printer 106, the overall system is capable of generating file formats employing TIFF, GIF, BMT, TGA, PCX, FLI, FLC, CUT, IMG and JPEG image compression formats. The system is capable of capturing images from 320×200 up to 640×480 resolution with 65,536 colors.

The base station computer 102 is thus able to directly control the videotape recorder and monitor 36 for playback and, together with tape position location or time stamping data maintained in the portable unit computer 32 and transferred via the RS232 data link 156, is able to rapidly and efficiently access particular video image frames captured by the videotape recorder and monitor 36 to facilitate the efficient generation of reports.

In the event a digital image storage device is employed in the mobile unit 20, such as an element of the mobile unit computer 32, digital images are directly downloaded to the base station computer 102, without employing a video frame grabber.

The base station computer 102 preferably includes a hard disk drive of at least 200 megabytes capacity. By way of example, a simple thermogram from a pyroelectric camera with 320×200 resolution results in a file size of 11K bytes. A single thermogram from a focal plane array camera, also 320×200 resolution, results in a typical file size of 30K bytes. A single black and white visual image of 320×200 resolution results in a typical file size of 42K bytes. A single color visual image of 320×200 resolution results in a typical file size of 310K bytes. A so-called slide, combining both visual and thermal images on one screen, of 320×200 resolution results in a file typically from 20 to 25K bytes in length. A single black and white visual image of 640×480 resolution results in a file typically 300K bytes in length.

In operation, the thermographer initially, employing software running in the base station computer 102, sets up an overall framework of the manner in which thermography is to be employed to monitor a plant. For example, templates for visual observation notes are established. Priority codes for prioritizing repairs are defined, as well as event forms which serve to prompt the thermographer to record all information needed to generate a final report in the event a fault is discovered. Location codes are defined which provide an approach for identifying fault location on equipment with large dimensions. Instruction codes are defined, attached to particular measurement points, which prompt the thermographer to use proper filters, lenses, distance, angle, and the like. Equipment types found in the plant are defined, such as motor control centers, transformers, pumps, and the like. Components found in the equipment are defined, such as fuses, circuit breakers, insulators, lightening arresters, and the like. Fault types which can be associated with the components are defined, and recommended actions that result from particular fault types are defined.

The results of defining these various items of information are described hereinbelow with reference to the example screens of FIGS. 3-18.

Prior to beginning data collection, this framework information is uploaded from the base station computer 102 to the mobile unit computer 32.

The thermographer then uses the mobile unit 20 to scan the plant, employing the infrared camera 28. Anomalous conditions (i.e. thermographic "events") are recorded in the videotape recorder 36, along with visual images acquired by means of the visual camera 30. The date/time of recording is recorded in the mobile unit computer 32, for later correlation with the date/time stamp recorded by the videotape recorder 36. The mobile unit computer 32, by means of the display screen 34, additionally prompts the thermographer for additional information needed to generate the final report, as is described hereinbelow by way of example with reference to FIGS. 3-18.

After data collection is completed, the thermographer again establishes communication between the base station computer 102 and the mobile unit computer 32, but this time data is transferred from the mobile unit computer 32 to the base station computer 102, which may be viewed as a host computer. The data thus transferred from the mobile unit computer 32 and the base station computer 102 via the RS232 multiplexer 110 and the data link 154 includes notes made by the thermographer during data collection and identifying information relating to particular thermographic images whereby the base station computer 102 is provided with information (e.g. tape position or date/time stamp) to enable access to particular video recorded images employing the LANC channel 39 of the videotape recorder 36.

Infrared and visual images are then captured as described above. Appropriate software is employed to manipulate captured images before storage, as well as for generating reports that combine images with text. The laser printer 106 enables printing of reports.

Accordingly, it will be appreciated that the process of thermographic data collection and report generation becomes highly automated, with a significant reduction in the amount of time required. Comprehensive documentation is produced, including "proof" of inspection at a particular date and time, which can result in a reduction in insurance premiums, depending on the particular plant.

Figure 3:
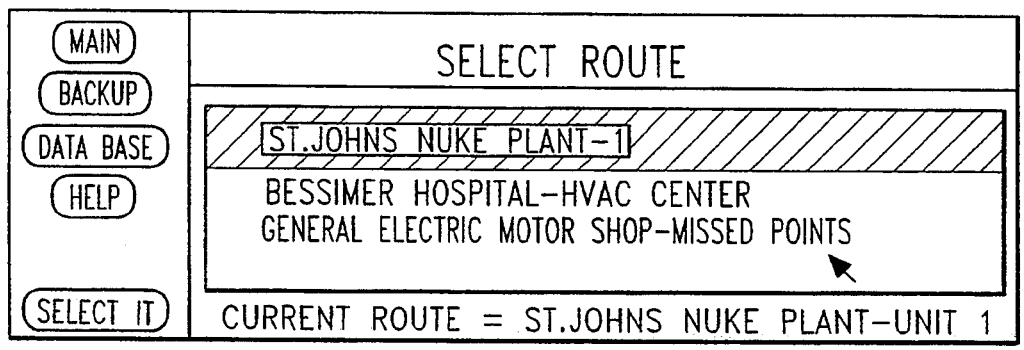
FIG. 3 is an example of a "select route" screen which may be presented on the display of the mobile unit data processing device.

Considering now exemplary screens which may be displayed on the display device 34 of the mobile unit computer 32, FIG. 3 illustrates a select route form which enables the thermographer to select which data collection route he desires to use.

Figure 4:
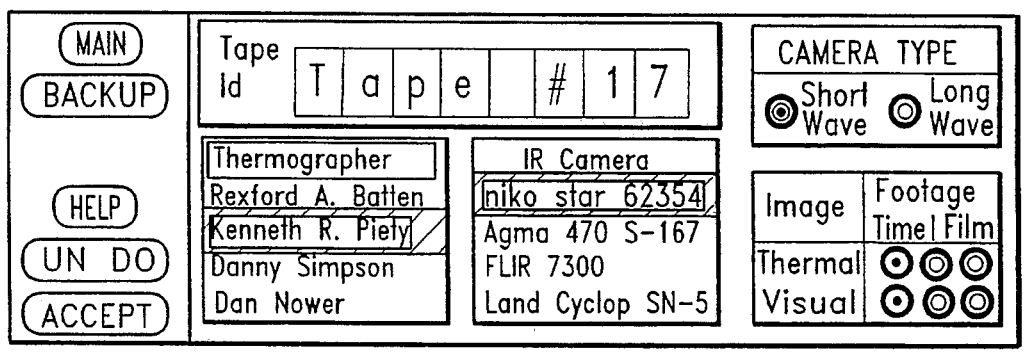
FIG. 4 is an example of a current user and equipment screen which may be presented on the display of the mobile unit data processing device.

FIG. 4 illustrates a current user and equipment form which is employed by the thermographer to enter in the tape ID, the name of the current thermographer, the particular infrared camera being used, the type of camera (either long or shortwave), and the image address type, either time, footage or film. All of this information facilitates later generation of a report.

Figure 5:
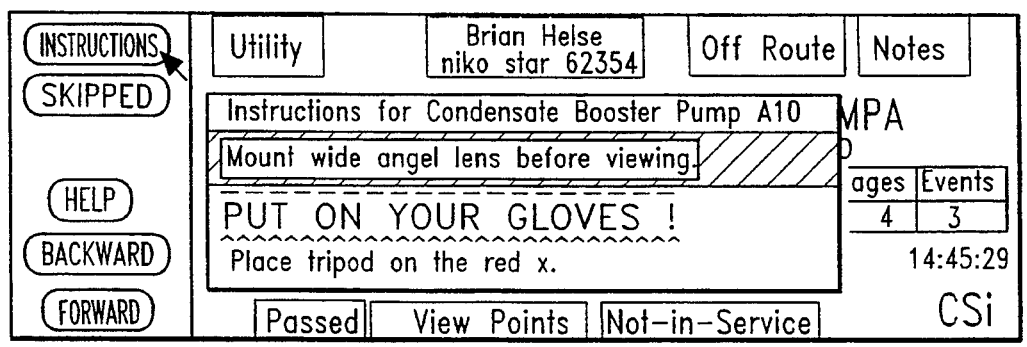
FIG. 5 is an example of a instruction screen which may be presented on the display of the mobile unit data processing device.

FIG. 5 is an example of a pop up list which contains instructions for the thermographer to follow when measuring a particular piece of equipment. In a preferred implementation, there can be up to twenty four lines of instructions, and the list can be scrolled.

FIG. 6 is an example of a point list form which leads the thermographer through a subsequent series of forms to enable complete documentation of a fault. The particular form illustrated in FIG. 6 is a fault location form where the user defines the location of the fault.

FIG. 7 illustrates an example of a faulty component form. Each type of equipment has its own customized list of components.

FIG. 8 illustrates an identify fault type form, which displays a list of fault types unique to a particular component type, presented after the component is selected.

As depicted in FIG. 9, the thermographer is next presented with a list of recommended actions based on the faulty component and fault type selected as just described.

As illustrated in FIG. 10, the thermographer can unmark any of these actions if they do not fit the fault. Additionally, the thermographer can add more actions to the list.

The thermographer next records the temperature and emissivity data pertaining to the fault, employing a form like that of FIG. 11. This form allows the thermographer to automatically measure and store data into various fields which, in this example, include exception temperature, reference temperature, and background temperature, as measurable fields.

Electrical and atmospheric conditions pertaining to a fault are relevant for documentation purposes, and are entered on a form like that of FIG. 12.

FIG. 13 illustrates an image parameter form which allows the user to enter in camera settings employed when taking the infrared image. Recording this information allows the thermographer to repeat image collection at a later date using the same parameters.

The mobile unit computer 32 may be programmed to calculate temperature rise and the percent full load, once all the data pertaining to a fault have been entered, and then provide an estimate of the severity of the fault condition. Such is shown in the exemplary screen of FIG. 14. The thermographer can assign a different priority to the fault if so desired.

The thermographer is not constrained by route information uploaded from the base station computer 102 to the mobile unit computer 32. FIGS. 15, 16, 17 and 18 represent a procedure for establishing a piece of "off route" equipment.

FIG. 15 illustrates a screen for entering a category for new off route equipment.

After selecting the category, in the example case Switchyard, the thermographer is presented with a screen like that of FIG. 16, which is a list of equipment types for that category.

After accepting one of these, the thermographer is presented with a screen like that of FIG. 17, where equipment ID and description are entered.

Figure 18:
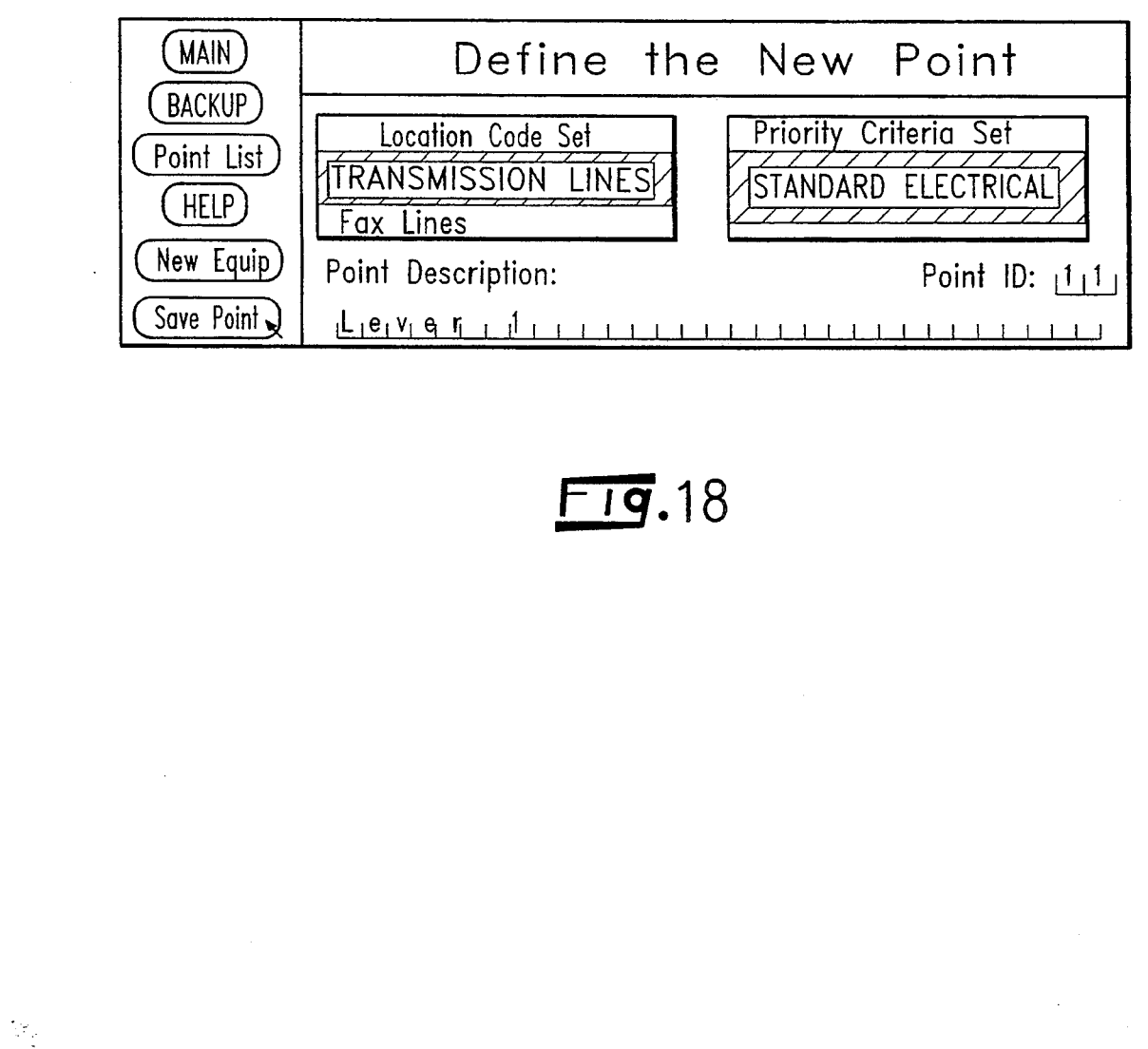

Finally, in FIG. 18, the thermographer is asked to enter in the point ID and description for the first point on the new equipment. The thermographer is also able to select the location code form and the priority code set to go with this point.

From the foregoing summary of example screens, it will be appreciated that the thermographer is prompted to enter complete and relevant documentation for particular faults, to be correlated with particular infrared and visual images, all of which facilitates rapid and essentially automatic generation of reports.

One aspect of the invention is that the mobile unit data processing device 32 prompts the thermographer towards particular problems possibly resulting from a particular thermographically-observed condition, somewhat like an "expert" system. Thus, a less experienced thermographer is enabled to produce useful reports.

FIGS. 19 and 20 are representative infrared fault flowcharts, respectively for a transformer controlled cubicle and for a motor control center cabinet, presenting, in a hierarchical tree form, information to be presented to the user as a series of menus on the display 38. Thus, within each component, the thermographer is prompted to observe particular subcomponents, both visually and employing infrared imaging, looking for particular faults and symptoms. When a particular fault is observed, the thermographer is provided with a recommendation of action to take, as well as the manner IN which the fault is to be reported.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A mobile infrared thermography unit comprising:
   an infrared camera;
   a visible image camera;
   a storage device for recording at least images;
   a switch for selectively connecting either said infrared camera or said visible image camera to said storage device for thermographic or visible image recording; and
   a data processing device interfaced to at least one of said infrared camera, said visible image camera and said storage device for at least maintaining a record of identifying information related to recorded images;
   said data processing device being interfaced to said switch for monitoring whether an infrared or a visible image is being recorded.

2. A mobile infrared thermography unit in accordance with claim 1, which further comprises a microphone connected to said storage device such that comments related to a particular thermographic or visible image may be recorded with the image.

3. A mobile infrared thermography unit in accordance with claim 1, wherein said data processing device includes a touch screen.

4. A mobile infrared thermography unit in accordance with claim 1, wherein said data processing device is operable to prompt a user to enter notes and to record user notes.

5. A mobile infrared thermography unit comprising:
   an infrared camera;
   a storage device for at least recording thermographic images captured by said infrared camera; and
   a data processing device including a display and operable to prompt a user of said unit through indications on said display regarding particular equipment to be thermographically inspected.

6. A mobile infrared thermography unit in accordance with claim 5, wherein said data processing device is further operable through indications on said display to suggest to a user at least one candidate problem indicated by a particular thermographically-observed condition.

7. A mobile infrared thermography unit in accordance with claim 5, wherein said data processing device is operable to prompt a user through indications on said display to enter notes and to record user notes employing predetermined templates.

8. A mobile infrared thermography unit in accordance with claim 5, wherein said data processing device includes a touch screen.

9. A mobile infrared thermography unit in accordance with claim 5, wherein said data processing device is interfaced to at least one of said infrared camera and said storage device for at least maintaining a record of identifying information related to recorded thermographic images.

10. A mobile infrared thermography unit in accordance with claim 5, which further comprises:
    a visible image camera; and
    a switch for selectively connecting either said infrared camera or said visible image camera to said storage device for image recording.

11. A mobile infrared thermography unit in accordance with claim 10, wherein said data processing device is interfaced to said switch for monitoring whether an infrared or a visible image is being recorded.

12. A mobile infrared thermography unit in accordance with claim 10, which further comprises a microphone connected to said storage device such that comments related to a particular thermographic or visible image may be recorded with the image.

13. A mobile infrared thermography unit in accordance with claim 5, which further comprise at least one interface between said data processing device and an external measurement instrument.

14. A mobile infrared thermography unit in accordance with claim 13, wherein the external measurement instrument comprises a temperature measuring device.

15. A mobile infrared thermography unit in accordance with claim 13, wherein the external measurement instrument comprises a current measuring device.

16. A mobile infrared thermography unit in accordance with claim 5, which further comprises a RMS AC current measurement interface to said data processing device.

17. A mobile infrared thermography unit in accordance with claim 5, which further comprises a voltage measurement interface to said data processing device.

18. A mobile infrared thermography unit in accordance with claim 5, wherein said data processing device is operable to prompt a user through indications on said display to record all information needed to generate a final report in the event a fault is discovered.

19. A mobile infrared thermography unit in accordance with claim 5, wherein said data processing device is operable to prompt a user through indications on said display with information selected from the group consisting of location information for fault location on equipment with large dimensions, and instruction information regarding camera setup for particular measurement points.

20. A mobile infrared thermography unit comprising:
an infrared camera;
a storage device for recording thermographic images captured by said infrared camera; and
a data processing device including a display and operable through indications on said display to suggest to a user at least one candidate problem indicated by a particular thermographically-observed condition.

21. An infrared thermography system comprising:
a base station;
a mobile thermographic unit at least selectably connectable to said base station;
said mobile thermographic unit including an infrared camera, a mobile unit storage device for at least recording thermographic images captured by said infrared camera and a mobile unit data processing device including a display and operable to prompt a user of said unit through indications on said display regarding particular equipment to be thermographically inspected; and
said base station including a base station data processing device operable, when said mobile thermographic unit is connected to said base station, to upload user prompting information to said mobile unit data processing device.

22. An infrared thermography system in accordance with claim 21, wherein said mobile unit data processing device is further operable through indications on said display to suggest to a user at least one candidate problem indicated by a particular thermographically-observed condition.

23. An infrared thermography system in accordance with claim 21, wherein said mobile unit data processing device is operable to prompt a user through indications on said display to enter notes and to record user notes employing predetermined templates.

24. An infrared thermography system in accordance with claim 21, wherein said mobile unit data processing device is operable to prompt a user through indications on said display to record all information needed to generate a final report in the event a fault is discovered.

25. An infrared thermography system in accordance with claim 21, wherein said mobile unit data processing device is operable to prompt a user through indications on said display with information selected from the group consisting of location information for fault location on equipment with large dimensions, and instruction information regarding camera setup for particular measurement points.

26. An infrared thermography system in accordance with claim 21, wherein said base station data processing device is further operable to prepare inspection reports based on equipment thermographically inspected by the user.

* * * * *

REEXAMINATION CERTIFICATE (3221st)

United States Patent [19]
Piety et al.

[11] B1 5,386,117
[45] Certificate Issued Jun. 10, 1997

[54] INFRARED THERMOGRAPHY SYSTEM INCLUDING MOBILE UNIT

[75] Inventors: Kenneth R. Piety; Brian D. Heise; Rexford A. Battenberg, all of Knoxville; Willie T. King, Powell, all of Tenn.

[73] Assignee: Computational Systems, Incorporated, Knoxville, Tenn.

Reexamination Request:
No. 90/004,188, Mar. 20, 1996

Reexamination Certificate for:
Patent No.: 5,386,117
Issued: Jan. 31, 1995
Appl. No.: 73,132
Filed: Jun. 7, 1993

[51] Int. Cl.$^6$ .................................................. G01N 25/72
[52] U.S. Cl. ........................................ 250/330; 250/358.1
[58] Field of Search ................................... 250/330, 332, 250/342, 358.1

[56] References Cited

U.S. PATENT DOCUMENTS

| | | | |
|---|---|---|---|
| 3,076,961 | 2/1963 | Bibbero | 343/6 |
| 3,591,713 | 7/1971 | Olsson et al. | 178/6.8 |
| 3,752,915 | 8/1973 | Parker et al. | 178/6.7 R |
| 3,933,044 | 1/1976 | Loper et al. | 73/355 R |
| 4,020,344 | 4/1977 | Kerschbaum | 250/330 |
| 4,365,307 | 12/1982 | Tatsuwaki et al. | 364/557 |
| 4,679,068 | 7/1987 | Lillquist et al. | 358/44 |
| 4,751,571 | 6/1988 | Lillquist et al. | 358/113 |
| 4,913,558 | 4/1990 | Wettervik et al. | 374/4 |

(List continued on next page.)

FOREIGN PATENT DOCUMENTS

| | | | |
|---|---|---|---|
| 53-116729 | 10/1978 | Japan | 348/164 |
| 53-118309 | 10/1978 | Japan | 348/164 |

(List continued on next page.)

OTHER PUBLICATIONS

Tesche et al., "Einsatzerprobung Einer Mobilen Infrarot-Thermografie-Einrichtung", Forschungsvorhaben Im Auftrag Des Bundesministers Für Forshung Und Technologie (BMFT), Abschlubbericht, Germany 1978, 89 pages.

Lucier, "Infrared Thermography as a Predictive Maintenance Tool", SPIE vol. 581, Thermosense VIII, 1986 pp. 112–115.

(List continued on next page.)

*Primary Examiner*—Edward J. Glick

[57] ABSTRACT

A system including a mobile infrared thermography unit and a base station for automating the collection of thermographic data and for facilitating the efficient generation of reports. The mobile infrared thermography unit includes an infrared camera, a storage device such as a videotape recorder for at least recording thermographic images captured by the infrared camera, and a mobile unit computer. The mobile unit computer includes a touch screen display for presenting information to a thermographer and for receiving data and command inputs from the thermographer. The mobile unit computer is interfaced to the infrared camera or the videotape recorder for maintaining a record, either by tape position or date/time stamp, where thermographic images of particular equipment are recorded. The mobile unit computer includes a display operable to prompt the thermographer with route information regarding particular equipment to be thermographically inspected, as well as to suggest to the thermographer particular problems possibly indicated by a particular thermographically-observed condition. The base station includes a base station computer which transfers information to the mobile unit computer prior to undertaking an inspection route, and receives information from the mobile unit computer when the route is completed. The base station computer is capable of directly accessing and downloading particular infrared images recorded by the videotape recorder, employing the tape position or date/time stamp information.

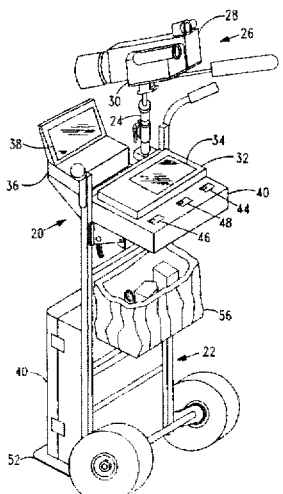

U.S. PATENT DOCUMENTS

| | | | |
|---|---|---|---|
| 4,967,276 | 10/1990 | Murakami et al. | 358/183 |
| 5,045,937 | 9/1991 | Myrick | 348/144 |
| 5,133,605 | 7/1992 | Nakamura | 374/124 |
| 5,159,198 | 10/1992 | Kohsaka et al. | 250/330 |
| 5,166,789 | 11/1992 | Myrick | 358/109 |
| 5,237,308 | 8/1993 | Nakamura | 340/588 |
| 5,445,157 | 8/1995 | Adachi et al. | 128/664 |

FOREIGN PATENT DOCUMENTS

| | | |
|---|---|---|
| 62-098227 | 5/1987 | Japan. |
| 63-058222 | 3/1988 | Japan. |
| 63-135871 | 6/1988 | Japan. |
| 63-235834 | 9/1988 | Japan. |
| 63-235835 | 9/1988 | Japan. |
| 63-238435 | 10/1988 | Japan. |
| 63-277942 | 11/1988 | Japan. |
| 64-001408 | 1/1989 | Japan. |
| 1240846 | 9/1989 | Japan. |
| 2017460 | 1/1990 | Japan. |
| 3154857 | 7/1991 | Japan. |
| 3197828 | 8/1991 | Japan. |
| 4104021 | 4/1992 | Japan. |

OTHER PUBLICATIONS

Burnay et al., "Applications of Thermal Imaging", Adam Hilger, Bristol and Philadelphia, 1988, pp. 46–85 and 156–161.

Grant, "Infrared Thermography—A Maintenance Tool", Paper Technology, vol. 30, No. 5, 1989, pp. V/19–V/20.

Ljungberg et al., "Comparison of Indoor and Vehicle–Borne Thermography", SPIE vol. 1313, Thermosense XII, 1990, pp. 92–99.

Heise, "Thermographic Programs and Technology" Computational System Inc., 1993, 18 pages.

Moshage et al., "Vibration Monitoring for Predictive Maintenance in Central Energy Plants", USACERL Technical Report FE–93/25, 1993, 11 pages.

Piety et al., "Practical Experience Using an Automated Diagnostic System", Sound and Vibration, vol. 27, No. 2, Feb. 1993, pp. 12–19.

Computational Systems Inc., Advertising Brochure, "Introducing CSI's Infrared Thermography System", 1993, 4 pages.

Maxtech International, Inc., "Company Briefs" in Infrared Imaging News, vol. 1, Issue 8, 1995, p. 7.

Piety et al., "A New Approach for Implementing a Computer–Based Predictive Maintenance Program" IEEE Trans. on Nuclear Science, vol. NS–32, No. 1 (Feb. 1985) pp. 1005–1006.

Piety et al., "Predictive Maintenance Programs for the Power Generation Industry" Sound and Vibration, vol. 20, No. 6 (Jun. 1986) pp. 18–21.

Bales, "Infrared Non–Destructive–Test Workstation" SPIE Proceedings, Infrared Imaging systems: Design, Analysis, Modeling, and Testing III, Apr. 23–24, 1992, vol. 1689 (1992) pp. 163–177.

Bales Scientific Inc. sales brochure "Bales Scientific Inc. Introduces The TIP System A True Infrared NDT Workstation" (1992).

Arro, "Evolution of Continuous Mobile Thermography for Large Scale Diagnostic Surveys" SPIE Proceedings, An International Conference on Thermal Infrared Sensing for Diagnostics and Control (Thermosense VI), Oct. 2–5, 1983 vol. 446, pp. 20–23.

Allen, "Mobile Infrared Thermography Surveys of Buildings Within a Community" SPIE Proceedings, An International Conference on Thermal Infrared Sensing for Diagnostics and Control (Thermosense X), Apr. 5–8, 1988 vol. 934, pp. 16–18.

Pardue et al. "Elements of Reliability–Based Machinery Maintenance," Sound and Vibration, vol. 26 No. 5, (May 1, 1992), pp. 14–20.

Proskurnicki et al. "Mobile diagnostics of electrical systems using expert–system based thermal analysis software." Proc. of the SPIE, vol. 934, International Conference on Thermal Infrared Sensing for Diagnostics and Control (Thermosense X) Apr. 5–8, 1988, pp. 139–154, 130.

Sales brochure AGEMA Superviewer (1986).

Sales brochure "Thermovision® 800 series TIC–8000 with CATS E" (1988).

Sales brochure "Heat made visible" (1989).

Sales brochure AVIO "Thermal Video System TVS–5000 Series" (1989).

Anonymous, "Improving Maintenance With Infrared", Maintenance Technology (Nov. 1989) reprint copyright 1989.

Sales brochure AGEMA Superviewer (1990).

Howard et al. "Imaging and the PS/2," Advanced Imaging, Jan. 1990 reprint.

infra/SOFT™ thermographic image processing system sales brochure, Engineered Data Systems Inc. copyright 1991.

Sales brochure "Insight 80 Series Thermal Imaging Camera" Insight Vision Systems, Inc. Mar. 1987.

Sales brochure "STARsight Thermal Imaging System" Insight Vision Systems, Inc. dated Aug. 23, 1991.

Sales brochure ISI Group Inc. VideoTherm 96 (Copyright 1991).

Sales brochure Inframetrics Model 600L (Apr. 1988 date code).

Sales brochure Inframetrics Model 522 (Aug. 1987 date code).

Inframetrics sales brochure "International Standard Thermal Imaging System" (Jan. 1986).

Hughes Aircraft Co. sales brochure "Color Television Thermography from Hughes, Probeye Thermal Video Systems" (Sep. 1986).

Hughes Aircraft Co. sales brochure "Probeye Series 3000 Thermal Video Systems" (May 1987).

Sales brochure "Everyone expects your utility to be perfect" (1990).

Sales brochure "Model 522L Thermal Imaging Radiometer" (Apr. 1991).

Sales brochure "Thermagram" (Nov. 1991).

Operating Manual Agema Thermovision® 480 series (Copyright 1992).

Infraspection Institute "IR/INFO '91" conference announcement, including Presentation of New Report Generation Software for Predictive Maintenance Applications presented by Paul Grover and Gary Howard at Las Vegas, Nevada conference, Oct. 31, 1991.

Infraspection Institute "Why Exception?" Infraspection Institute Newsletter (dated Spring 1992).

Infraspection Institute User's Manual "Exception Report Generation Software" (Copyright 1992).

Infraspection Institute sales brochure "Exception Report Generation System" (1992).

Infraspection Institute sales brochure "Exception IR Report Generation System" (1993).

Infraspection Institute Press Release "Exception Report Generation Software Version 3.0" Feb. 24, 1993.

John Reason, ed. "Preventive Maintenance; Customized van speeds infra–red inspections" Electrical World (Jul. 1992) reprint.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–4 and 20 is confirmed.

Claims 5–7, 9, 18, 19 and 21–25 are determined to be patentable as amended.

Claims 8, 10–17 and 26, dependent on an amended claim, are determined to be patentable.

New claims 27 and 28 are added and determined to be patentable.

5. A mobile infrared thermography unit comprising:
an infrared camera;
a storage device for at least recording thermographic images captured by said infrared camera; and
a data processing device including a display and operable *to store a predefined route of equipment and* to prompt a user of said unit *through the route* through indications on said display regarding particular equipment to be thermographically inspected.

6. A mobile infrared thermography unit in accordance with claim 5, wherein said data processing device is further operable through indications on said display to suggest to a user at least one candidate problem indicated by a particular thermographically-observed condition *specific to particular equipment on the predefined route*.

7. A mobile infrared thermography unit in accordance with claim 5, wherein said data processing device is operable to prompt a user through indications on said display to enter notes and to record user notes employing predetermined templates *specific to particular equipment on the predefined route*.

9. A mobile infrared thermography unit in accordance with claim 5, wherein said data processing device is interfaced to at least one of said infrared camera and said storage device for [at least] *recording identifying information with specific thermographic images stored in said storage device and* maintaining a *separate* record of *the* identifying information [related to recorded thermographic images] *such that specific stored thermographic images can subsequently be accessed for generating reports*.

18. A mobile infrared thermography unit in accordance with claim 5, wherein said data processing device is operable to prompt a user through indications on said display to record all information *specific to particular equipment on the predefined route* needed to generate a final report in the event a fault is discovered.

19. A mobile infrared thermography unit in accordance with claim 5, wherein said data processing device is operable to prompt a user through indications on said display with information selected from the group consisting of location information for fault location on equipment with large dimensions, and instruction information regarding camera setup for particular measurement points *specific to particular equipment on the predefined route*.

21. An infrared thermography system comprising:
a base station;
a mobile thermographic unit at least selectably connectable to said base station;
said mobile thermographic unit including an infrared camera, a mobile unit storage device for at least recording thermographic images captured by said infrared camera and a mobile unit data processing device including a display and operable *to store a predefined route of equipment and* to prompt a user of said unit *through the route* through indications on said display regarding particular equipment to be thermographically inspected; and
said base station including a base station data processing device operable, when said mobile thermographic unit is connected to said base station, to upload user prompting information to said mobile unit data processing device.

22. An infrared thermography system in accordance with claim 21, wherein said mobile unit data processing device is further operable through indications on said display to suggest to a user at least one candidate problem indicated by a particular thermographically-observed condition *specific to particular equipment on the predefined route*.

23. An infrared thermography system in accordance with claim 21, wherein said mobile unit data processing device is operable to prompt a user through indications on said display to enter notes and to record user notes employing predetermined templates *specific to particular equipment on the predefined route*.

24. An infrared thermography system in accordance with claim 21, wherein said mobile unit data processing device is operable to prompt a user through indications on said display to record all information *specific to particular equipment on the predefined route* needed to generate a final report in the event a fault is discovered.

25. An infrared thermography system in accordance with claim 21, wherein said mobile unit data processing device is operable to prompt a user through indications on said display with information selected from the group consisting of location information for fault location on equipment with large dimensions, and instruction information regarding camera setup for particular measurement points *specific to particular equipment on the predefined route*.

27. *A mobile infrared thermography unit for collecting thermographic data in the field comprising:*
   *an infrared camera;*
   *storage means for recording thermographic images captured by said infrared camera, for storing a plurality of predefined routes, each route defining pieces of eqiupment, for storing identifying information for each piece of equipment including information as to type, inspection points and name of each piece of equipment; and*
   *a data processing device including a display and operable:*
      *to select one of the routes for inspection in response to user commands,*
      *to prompt a user through indications on said display regarding particular equipment to be thermographically inspected, the particular equipment being defined by the selected route,*
      *to prompt a user to provide location information in a predefined format and to select one of a predefined* set of potentially faulty components, said location information and said set of potentially faulty components being dependent upon and based upon the type of the particular piece of equipment being inspected, and to prompt a user to select a fault type from a predefined set of candidate fault types, said set of candidate fault types being based upon the identity of the faulty component that was selected by the user.

28. A mobile infrared thermography unit for collecting thermographic and video data in the field relating to equipment and suspected faults in the equipment comprising:

an infrared camera;

storage means for recording thermographic images captured by said infrared camera, and for storing identifying information for each piece of equipment to be inspected including information as to type of each piece of equipment; and a data processing device including a display and operable:

to prompt a user through indications on said display regarding particular equipment to be thermographically inspected, and to prompt a user through indications on said display to make selections from a sequential hierarchy of selection sets containing suggestions related to the type of equipment being inspected and the suspected fault, the hierarchy including higher order selection sets that are presented to the user before lower order selection sets, the hierarchy being defined such that the content of the lower order selection sets is dependent in part on the selections made in the higher order selection sets.

* * * * *